(12) United States Patent
Freed et al.

(10) Patent No.: US 11,053,037 B2
(45) Date of Patent: Jul. 6, 2021

(54) SYSTEM AND METHOD FOR PURGING OXYGEN FROM MEDICAL VIALS

(71) Applicant: Insys Development Company, Inc., Chandler, AZ (US)

(72) Inventors: Simon Freed, Round Rock, TX (US); David C. Woodruff, South Lebanon, OH (US)

(73) Assignee: HIKMA PHARMACEUTICALS USA INC., Eatontown, NJ (US)

( * ) Notice: Subject to any disclaimer, the term of this patent is extended or adjusted under 35 U.S.C. 154(b) by 59 days.

(21) Appl. No.: 16/116,020

(22) Filed: Aug. 29, 2018

(65) Prior Publication Data

US 2019/0106232 A1 Apr. 11, 2019

Related U.S. Application Data

(60) Provisional application No. 62/569,161, filed on Oct. 6, 2017.

(51) Int. Cl.
*B65B 31/04* (2006.01)
*B65B 7/28* (2006.01)
(Continued)

(52) U.S. Cl.
CPC ............ *B65B 31/041* (2013.01); *B65B 3/003* (2013.01); *B65B 7/2821* (2013.01);
(Continued)

(58) Field of Classification Search
CPC ... B65B 31/041; B65B 31/042; B65B 31/046; B65B 31/027; B65B 3/003; B67C 2003/2688
(Continued)

(56) References Cited

U.S. PATENT DOCUMENTS

| 3,332,788 A * | 7/1967 | Barnby ...................... B01L 3/56 422/547 |
| 5,201,165 A * | 4/1993 | Marano ................. B65B 31/041 53/432 |

(Continued)

*Primary Examiner* — Valentin Neacsu (74) *Attorney, Agent, or Firm* — Wood, Phillips, Katz, Clark & Mortimer (57) ABSTRACT

A medical vial filling system is adapted to fill a medical vial with a solution and cap the filled medical vial. A purging system includes a manifold disposed between a filling station and a capping station. The manifold includes a filling inlet port and a plurality of output ports. The output ports are positioned in a space proximate the filling station and in a space over the transport mechanism. A stoppering block includes a capping chamber for receiving a bushing positioned at the capping station. The stoppering block comprises a stoppering inlet port, a first nozzle opening into the capping chamber and a second nozzle extending into the capping chamber and directed into the medical vial when the medical vial is position in the capping station. A supply of non-reactive gas at the filling inlet port directs flow of the non-reactive gas out the manifold outlet ports to evacuate air and substitute the non-reactive gas in the filled medical vial and at the stoppering inlet port directs flow of the non-reactive gas in a flood zone surround a space above the medical vials when the medical vial is positioned in the capping station and in a stream directed into the medical vial when the medical vial is positioned in the capping station.

5 Claims, 9 Drawing Sheets

(51) Int. Cl.
*B65B 3/00* (2006.01)
*B65B 55/10* (2006.01)
*B65B 55/02* (2006.01)
*B65B 31/02* (2006.01)
*B67C 7/00* (2006.01)

(52) U.S. Cl.
CPC ......... *A61L 2202/23* (2013.01); *B65B 31/027* (2013.01); *B65B 31/042* (2013.01); *B65B 31/046* (2013.01); *B65B 55/027* (2013.01); *B65B 55/10* (2013.01); *B67C 7/0086* (2013.01)

(58) Field of Classification Search
USPC .......................................... 53/432, 471, 510
See application file for complete search history.

(56) References Cited

U.S. PATENT DOCUMENTS

| | | | | |
|---|---|---|---|---|
| 5,961,000 A * | 10/1999 | Sanfilippo | ............... | B65B 31/00 141/47 |
| 6,032,438 A * | 3/2000 | Sanfilippo | ............... | B65B 31/00 141/129 |
| 6,164,044 A * | 12/2000 | Porfano | ................. | B65B 55/10 422/28 |
| 6,231,907 B1 * | 5/2001 | Kino | ....................... | A23F 3/163 426/131 |
| 6,333,044 B1 * | 12/2001 | Santus | .................... | A61P 25/04 424/434 |
| 7,484,345 B2 * | 2/2009 | Woods | .................... | B65B 3/003 53/266.1 |
| 7,490,453 B2 * | 2/2009 | Py | .......................... | B65B 3/022 53/425 |
| 7,874,129 B2 * | 1/2011 | Py | .......................... | B65B 3/022 53/452 |
| 8,181,431 B2 * | 5/2012 | Py | .......................... | B65B 3/022 53/452 |
| 8,277,781 B2 | 10/2012 | Whiting et al. | | |
| 8,551,454 B2 | 10/2013 | Whiting et al. | | |
| 8,596,029 B2 * | 12/2013 | Pedmo | .................... | B65B 31/00 53/432 |
| 9,783,326 B2 * | 10/2017 | Py | ....................... | A61M 5/1782 |
| 2002/0110493 A1 * | 8/2002 | Dales | ................ | B01F 15/00357 422/534 |
| 2004/0256026 A1 * | 12/2004 | Py | .......................... | B29C 66/71 141/329 |
| 2006/0231157 A1 * | 10/2006 | Marcus | ................. | B65B 31/041 141/85 |
| 2007/0056251 A1 * | 3/2007 | Ruppman | ............. | B65B 31/041 53/510 |
| 2007/0119121 A1 * | 5/2007 | Woods | ....................... | B65B 3/30 53/268 |
| 2008/0289299 A1 * | 11/2008 | Mansson | ................. | B65B 31/00 53/403 |
| 2009/0013645 A1 * | 1/2009 | Mastio | .................... | A61L 2/087 53/425 |
| 2009/0145089 A1 * | 6/2009 | Py | .......................... | B65B 3/022 53/452 |
| 2009/0317295 A1 * | 12/2009 | Yonesu | .................... | H05H 1/46 422/29 |
| 2010/0233024 A1 * | 9/2010 | Whiting | ............... | A61K 31/407 422/41 |
| 2012/0222774 A1 * | 9/2012 | Husnu | ................... | A61J 1/1406 141/69 |
| 2013/0186391 A1 * | 7/2013 | Whiting | ............... | A61K 31/407 128/200.21 |
| 2014/0352265 A1 * | 12/2014 | Py | .......................... | B65B 51/00 53/468 |
| 2016/0068283 A1 * | 3/2016 | Py | .......................... | B65B 3/003 53/425 |
| 2017/0361966 A1 * | 12/2017 | Havel | .................... | B65B 3/003 |
| 2018/0065768 A1 * | 3/2018 | Won | ....................... | B65B 43/52 |

* cited by examiner

SYSTEM AND METHOD FOR PURGING OXYGEN FROM MEDICAL VIALS

BACKGROUND OF THE INVENTION

Field of the Invention

This application relates to filling of medical vials and, more particularly, to purging oxygen from medical vials.

Background of the Invention

Figure 1:
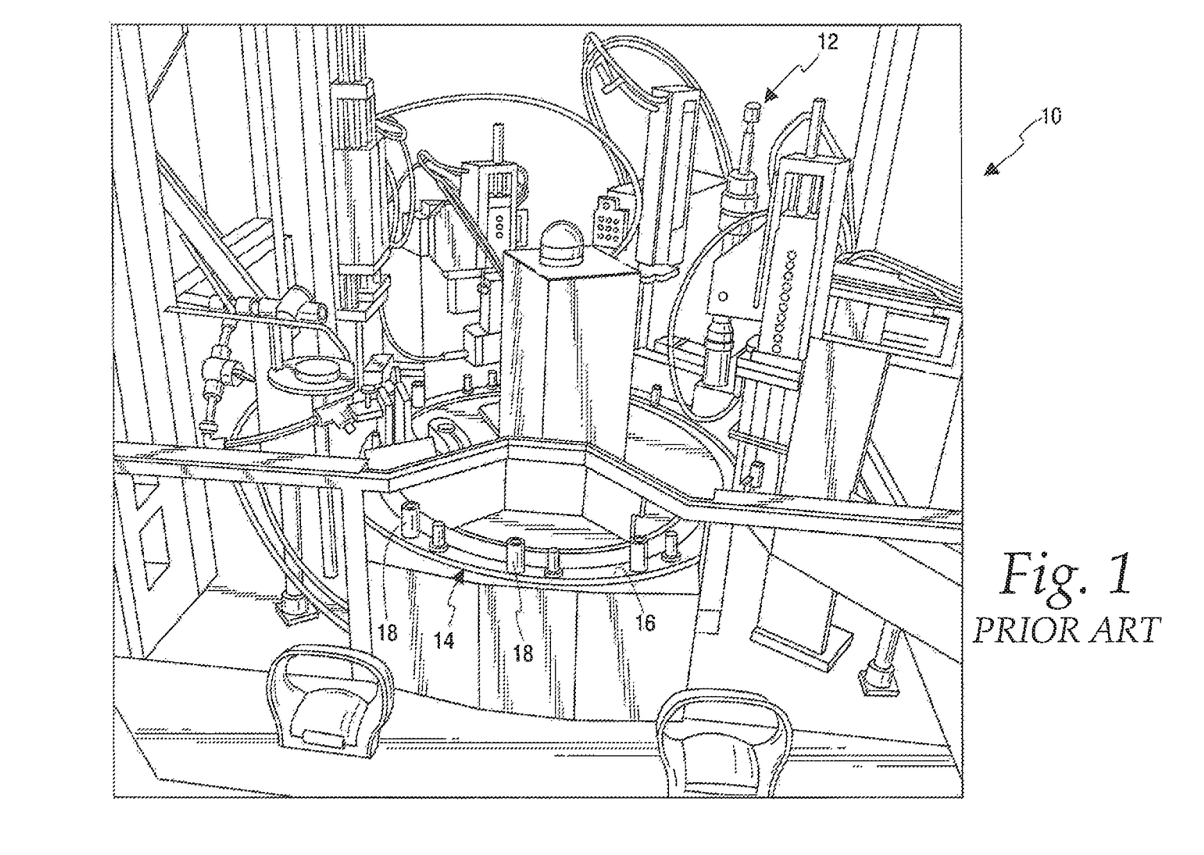
FIG. 1 is a perspective view of a prior art medical vial filling system adapted to fill a medical vial with a solution and cap the filled medical vial.
Figure 2:
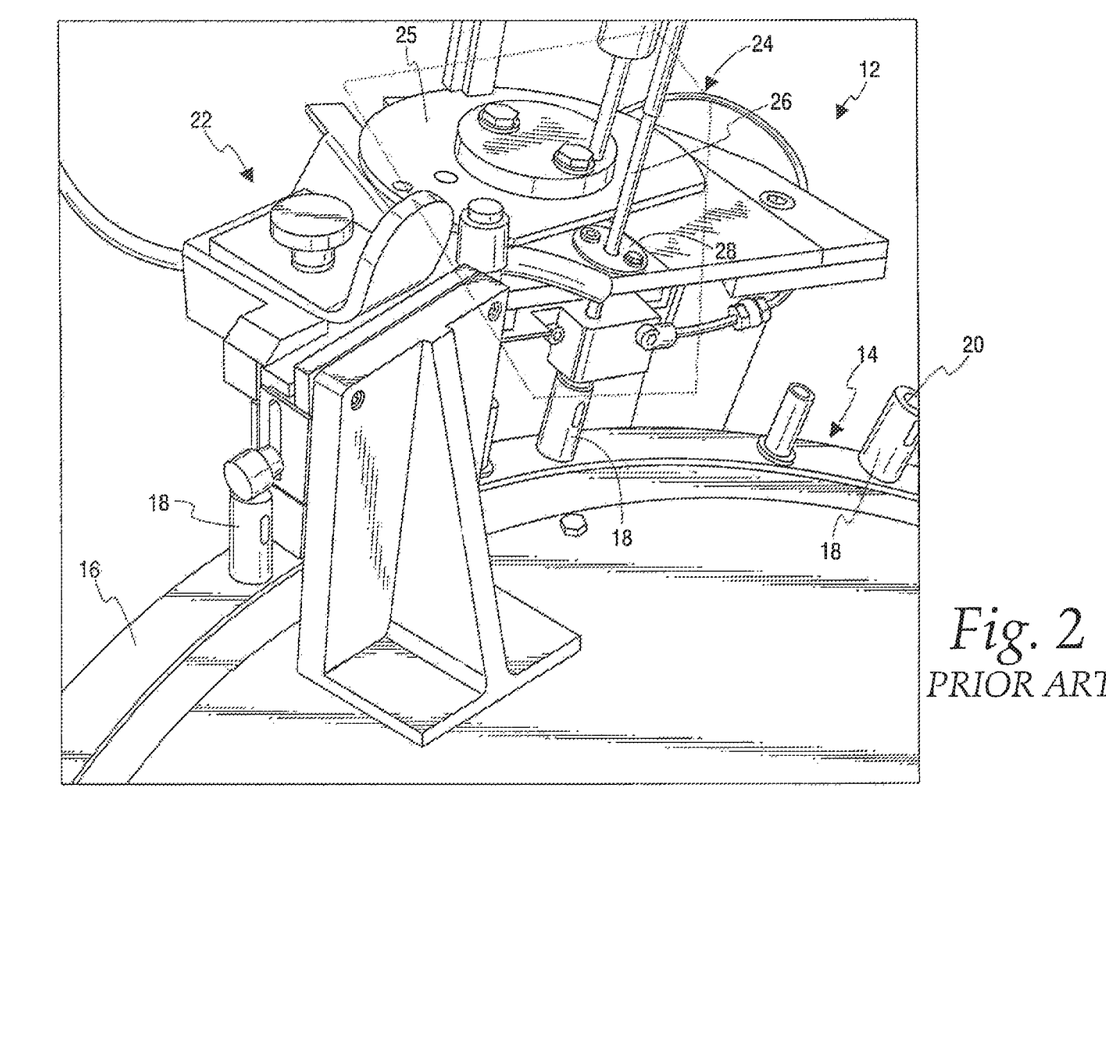
FIG. 2 is a partial perspective view of the medical vial filling system of FIG. 1 particularly illustrating a filling station and a capping station.

Various apparatus are available to fill medical vials with a desired solution. An exemplary filling system 10 is illustrated in FIG. 1 and comprises a rotary dial machine 12. The rotary dial machine 12 comprises a rotary transport mechanism 14 including a circular rail 16 supporting a plurality of bushings 18 circumferentially spaced around the rail 16. Each bushing 18 includes an upwardly facing opening 20 for selectively receiving a medical vial to be filled. The rotary transport mechanism 14 intermittently rotates the rail 16 to index the bushings 18 to a plurality of operating stations. Of relevance herein are a filling station 22 and a capping station, surrounded by an outline 24, see FIG. 2. The filling station 22 is adapted to fill the medical vial with a solution. The capping station 24 includes a supply mechanism 25 that is indexed to deliver an inert plug (not shown) into a funnel 28. A plunger 26 is driven downwardly into the funnel 28 to force the plug into the filled vial received in the bushing 18.

The rotary dial machine 12, while indexing the bushings 18, selectively lifts the bushings 18 and thus the vials, in any known manner, for various operations to be performed after manually loading a vial. The exemplary filling system 10 includes about twelve operating stations. Circumferential spacing between the bushings 18 is on the order of 6".

During the filling process, the open vial is surrounded with ambient air. Oxygen is a reactive gas and oxygen present in the vial at the time of capping can degrade the solution over time. It is desirable to purge the oxygen from the vial and replace it with a non-reactive gas, such as nitrogen.

Various apparatus are available for replacing oxygen with nitrogen. Typically, such apparatus provides a stream of non-reactive gas passed over the vial or into the vial prior to or subsequent to filling the vial with a solution. However, the purging of the oxygen may not be sufficient. Moreover, during subsequent processing steps the oxygen from ambient air may return to the vial during or prior to the capping operation.

The present application is directed to improvements in purging of oxygen from a medical vial and replacing it with a non-reactive gas, such as nitrogen.

SUMMARY OF THE INVENTION

As described herein, a system and method are provided for purging oxygen from filled medical vials.

There is disclosed in accordance with one aspect, a method to purge oxygen and substitute a non-reactive gas in a medical vial. The method comprises providing a medical vial filling system adapted to transfer a medical vial between a filling station that fills the medical vial with a solution and a capping station that inserts a plug in the filled medical vial. A flow of non-reactive gas is directed in a space above and around the medical vial when the medical vial is positioned in the filling station. A flow of the non-reactive gas is directed into an enclosed space through which the medical vial passes while being transferred between the filling station and the capping station. A flow of the non-reactive gas is directed in a flood zone surrounding a space above the medical vials when the medical vial is positioned in the capping station and in a nozzle stream directed into the medical vial when the medical vial is position in the capping station.

It is a feature that volume of the non-reactive gas in the flood zone to volume of the non-reactive gas in a nozzle stream is in a ratio of at least 3 to 1, and preferably in a ratio of about 5 to 1.

It is another feature that directing a flow of non-reactive gas in a space above and around the medical vial when the medical vial is positioned in a filling station comprises the medical vial filling system including a manifold defining a filling chamber having outlet ports dispensing the non-reactive gas. The medical vial filling system may lift the medical vial into the filling chamber and includes a filling nozzle for dispensing the solution into the medical vial while the non-reactive gas is dispersed in the filling chamber.

It is still another feature that directing a flow of the non-reactive gas in an enclosed space comprises providing a manifold disposed between the filling station and the capping station. The manifold includes a filling inlet port and a plurality of outlet ports. The outlet ports are positioned in a space over which the medical vial is transferred.

It is a further feature that the medical vial filling system comprises a stoppering block at the capping station and includes a capping chamber for receiving the medical vial positioned at the capping station. The stoppering block comprises a stoppering inlet port, a first nozzle opening into the capping chamber and a second nozzle extending into the capping chamber and directed into the medical vial when the medical vial is positioned in the capping station to provide the flood zone and the nozzle stream.

There is disclosed in accordance with another aspect a method to purge oxygen and substitute a non-reactive gas in a medical vial comprising providing a medical vial filling system adapted to transfer a medical vial between a filling station that fills the medical vial with a solution and a capping station that inserts a plug in the filled medical vial. The method provides a manifold in the medical vial filling system disposed between the filling station and the capping station. The manifold includes an inlet port and a plurality of outlet ports. The outlet ports are positioned in a space above and around the medical vial when the medical vial is positioned in the filling station and in an enclosed space through which the medical vial passes while being transferred between the filling station and the capping station. The method provides a supply of non-reactive gas at the inlet port whereby the non-reactive gas flows out the manifold outlet ports to evacuate oxygen and substitute the non-reactive gas in the filled medical vial.

There is disclosed in accordance with a further aspect a medical vial filling system adapted to fill a medical vial with a solution and cap the filled medical vial. The system comprises a transport mechanism including a plurality of bushings, each for selectively carrying a medical vial, in use, between a filling station that fills the medical vial with a solution and a capping station that inserts a plug in the filled medical vial. A manifold is disposed between the filling station and the capping station. The manifold includes a filling inlet port and a plurality of output ports. The output ports are positioned in a space proximate the filling station and in a space over the transport mechanism. A stoppering block includes a capping chamber for receiving a bushing positioned at the capping station. The stoppering block comprises a stoppering inlet port, a first nozzle opening into the capping chamber and a second nozzle extending into the capping chamber and directed into the medical vial when the medical vial is position in the capping station. A supply of non-reactive gas at the filling inlet port directs flow of the non-reactive gas out the manifold outlet ports to evacuate air and substitute the non-reactive gas in the filled medical vial, and a supply of non-reactive gas at the stoppering inlet port directs flow of the non-reactive gas in a flood zone surround a space above the medical vials when the medical vial is positioned in the capping station and in a stream directed into the medical vial when the medical vial is positioned in the capping station.

Further features and advantages of the invention will be readily apparent from the specification and from the drawings.

DETAILED DESCRIPTION OF THE INVENTION

Figure 3:
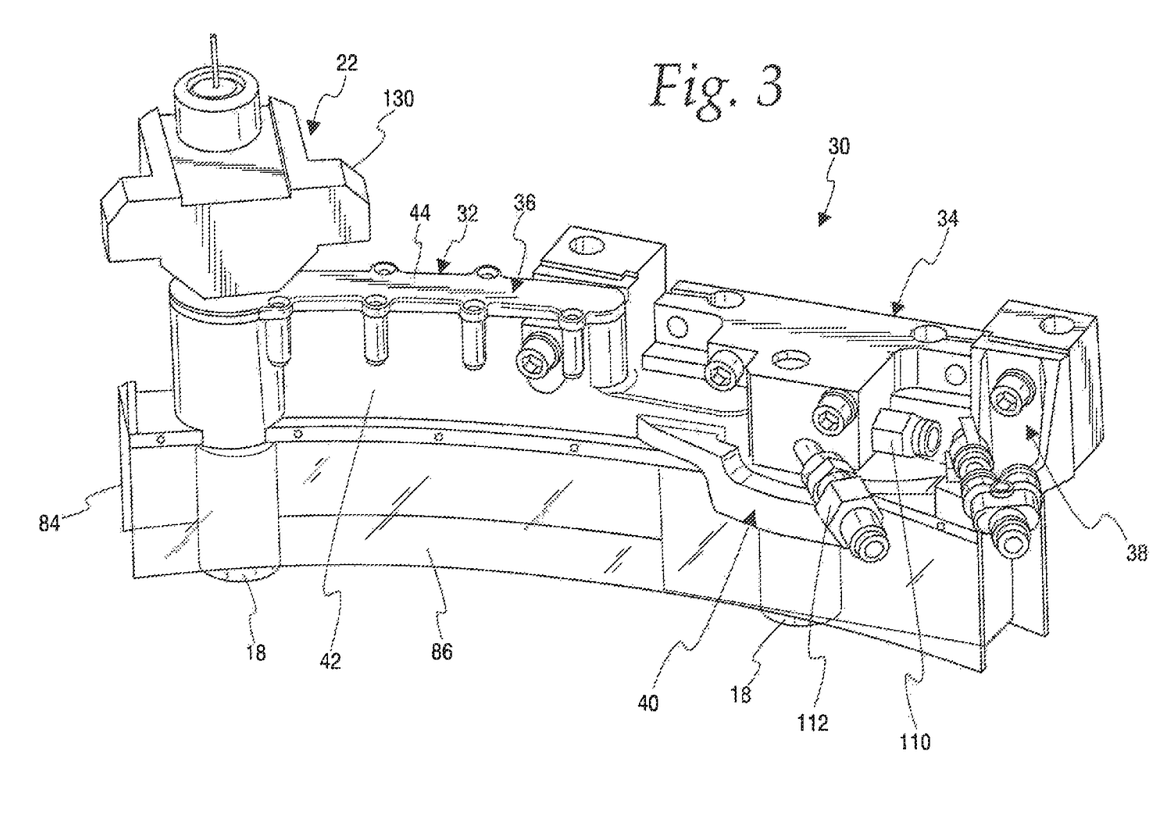
FIG. 3 is a perspective view of a purging apparatus adapted to be used with the medical vial filling system of FIGS. 1 and 2 for purging oxygen from medical vials during filling.
Figure 4:
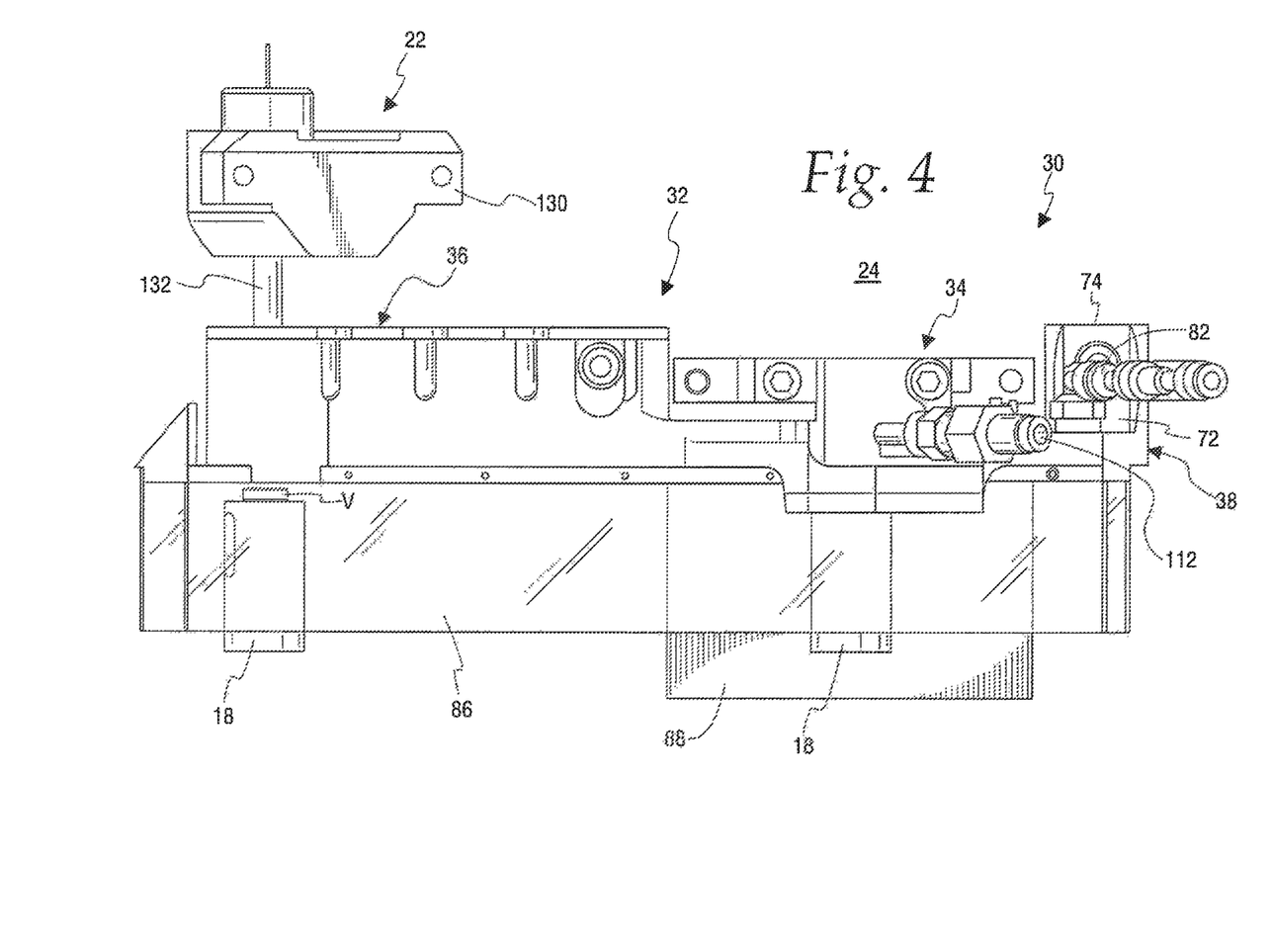
FIG. 4 is an elevation view of the purging apparatus of FIG. 3 as viewed from inside the machine's rotary transport mechanism, looking outward.
Figure 5:
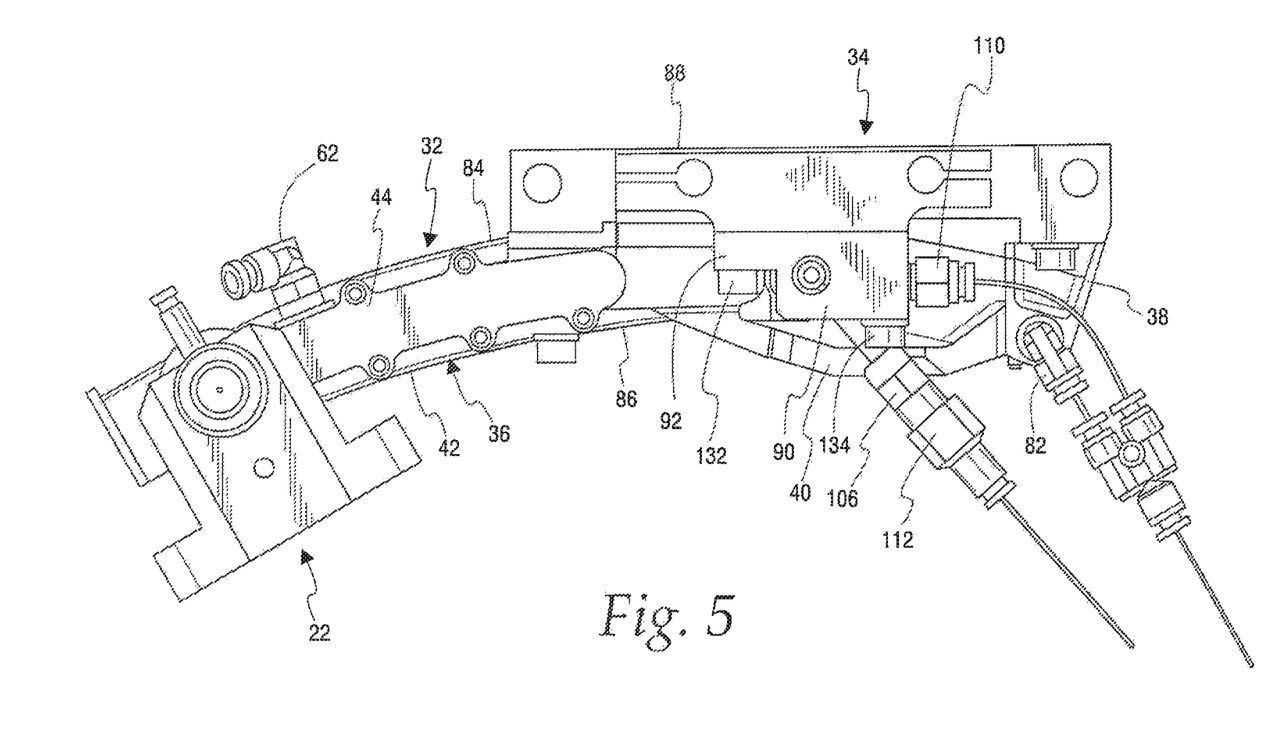
FIG. 5 is a plan view of the purging apparatus of FIG. 3.

This application is directed to a purging system 30, see FIGS. 3-5, adapted for use with the rotary dial machine 12 of FIG. 1 for purging oxygen content from medical vials. The purging system 30 comprises a manifold assembly 32 and a stoppering block 34. The manifold assembly 32 extends from the filling station 22 to the capping station 24. The stoppering block 34 is positioned at the capping station 24, as described below.

The purging system 30 is sized and shaped for the exemplary filling system 10 of FIG. 1. Particularly, the purging apparatus conforms to the radius and length of the circular rail 16 relative to the filling station 22 and the capping station 24. The size and shape may be adapted as is necessary in accordance with specifications of a filling system with which it may be used. The invention is not intended to be limited to a particular form of filling system.

The manifold assembly 32 comprises a first manifold 36 and a second manifold 38 connected by a bridge 40. Each manifold 36 and 38 comprises a hollow plastic body designed to distribute nitrogen to select areas of the filling system 10, as described more specifically below. The bridge 40 is also hollow. As such, the bridge 40 connects the interior space of the first manifold 32 with the interior space of the second manifold 38. The manifold assembly 32 is arcuate shaped corresponding to the curvature of the circular rail 16.

Figure 6:
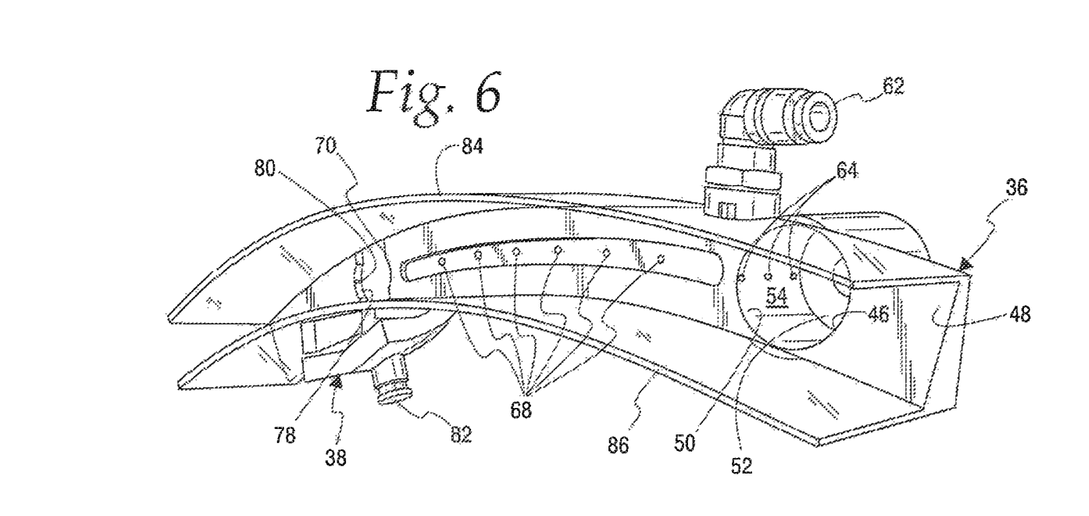
FIG. 6 is a bottom perspective view of a manifold of the purging apparatus.
Figure 7:
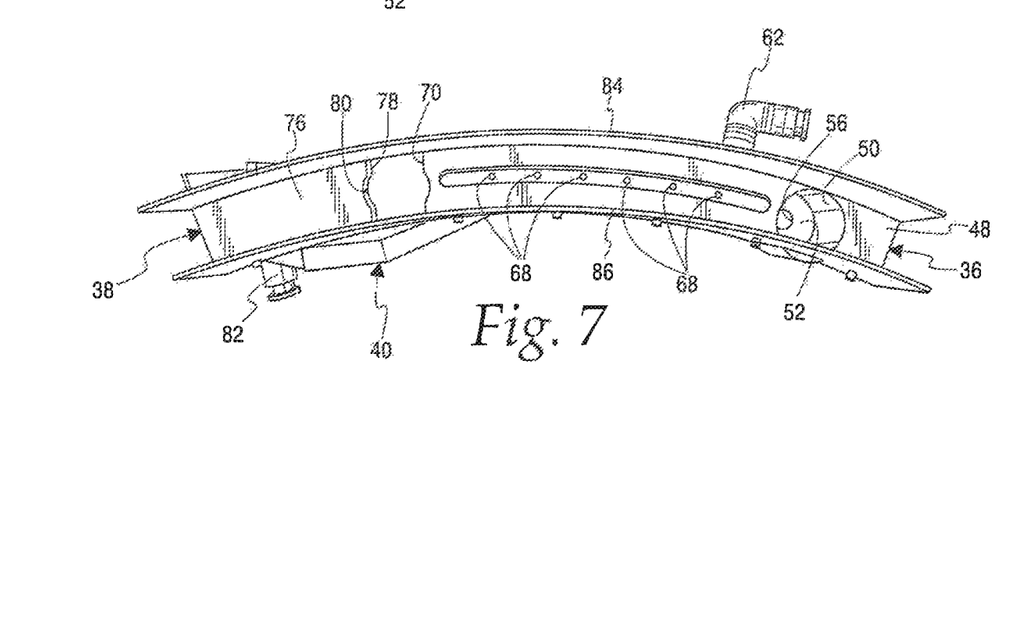
FIG. 7 is a bottom plan view of the manifold.
Figure 8:
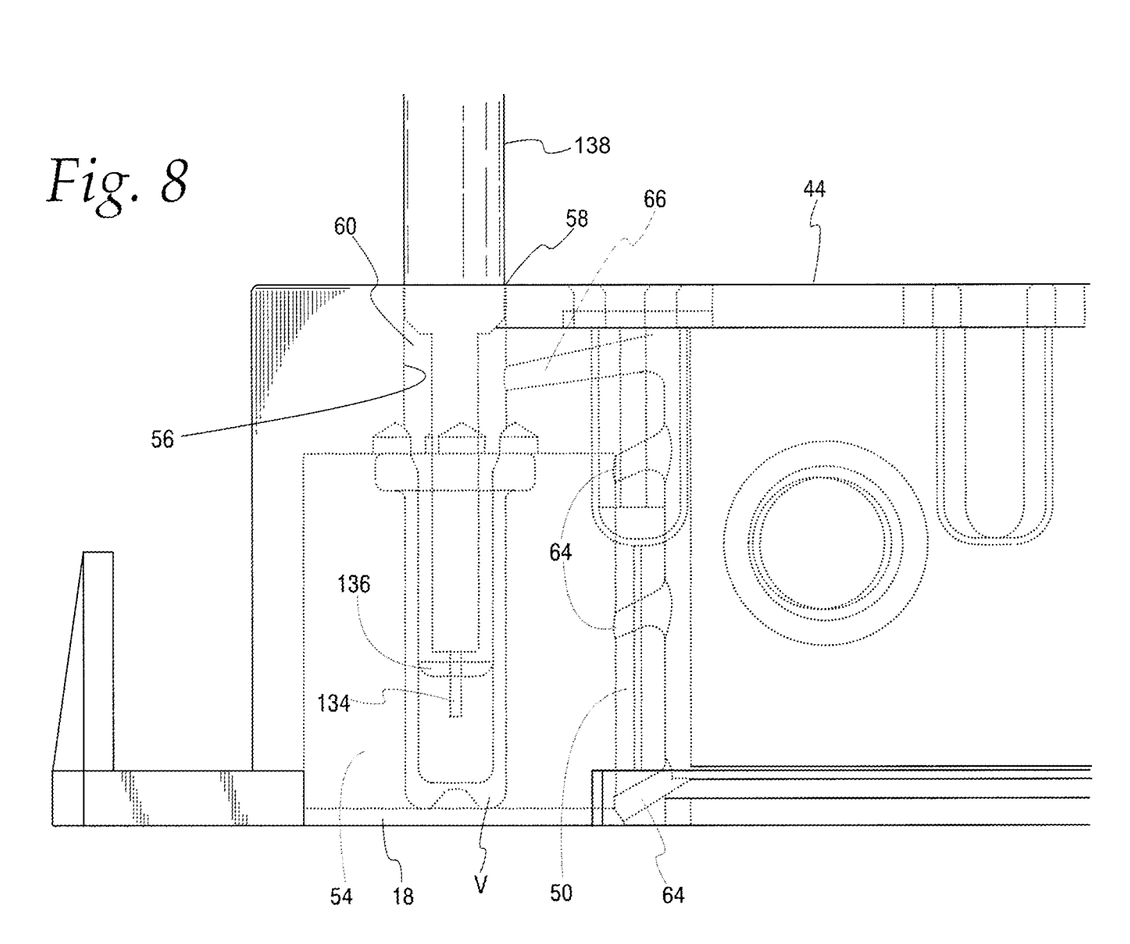
FIG. 8 is a partial isometric view of the manifold particularly illustrating purging performed at a filling chamber.

Referring also to FIGS. 5-7, the first manifold 36 includes a peripheral side wall 42 closed by a top wall 44 and a bottom wall 48. The bottom wall 48 includes a filling station opening 46. A lower cylindrical wall 50 extends upwardly from the bottom wall 48, within the peripheral wall 42, at the filling station opening 46 to an annular top wall 52 to define a lower filling chamber 54. A narrower upper cylindrical wall 56 extends upwardly from the annular wall 52 to an opening 58 in the top wall 44, see FIG. 8. The upper cylindrical wall 56 defines an upper filling chamber 60.

As discussed more particularly below, the lower filling chamber 54 is of a size and shape to receive the bushing 18. The upper filling chamber 60 is of a size to receive filling apparatus, as described below.

The first manifold sidewall 42 has an inlet port 62 for connection to supply of a non-reactive gas, such as nitrogen or an inert gas, as appropriate. The inlet port 62 opens to the interior space of the first manifold 36. A plurality of first filling station outlet ports 64 are provided in the lower cylindrical wall 50 opening into the lower filling chamber 54. An additional filling station outlet port 66 is in the upper cylindrical wall 56 and opens into the upper filling chamber 60, see FIG. 8.

The first manifold 36 also includes a plurality of spaced apart downwardly opening transfer outlet ports 68 in the bottom wall 48. The transfer outlet ports 68 are disposed between the filling station opening 46 and a capping station end 70 of the bottom wall 48.

The filling station outlet ports 64 and 66 are adapted to direct the flow of the non-reactive gas in a space above and around a medical vial when the medical vial is positioned in the filling station 22. The transfer outlet ports 68 are adapted to direct a flow of the non-reactive gas in an enclosed space through which the medical vial passes while being transferred between the filling station 22 and the capping station 24.

The second manifold 38 is positioned on an opposite side of the capping station 24, relative to the first manifold 36. The second manifold housing 36 includes a perimeter wall 72 closed by a top wall 74 and a bottom wall 76. The bottom wall 76 terminates at a capping station end 78 spaced from the first manifold capping station end 70. The space between the ends 70 and 78 is corresponds to position of the medical vial when it is located at the capping station 24, as described below. The bottom wall end 78 includes an outlet port 80. The second manifold 38 includes an inlet port 82. A similar outlet port could be provided in the first manifold end wall 70 to provide some purging of oxygen proximate the capping station 24. However, these alone are not sufficient to maintain the purge during the capping operation.

A pair of access panels 84 and 86 extend downwardly from the manifolds 36 and 38 for the length of the purging system 30. The access panels 84 and 86 may be transparent and extend downward to substantially enclose the space through which the bushings 18 pass while positioned in and between the filling station 22 and the capping station 24. A mounting bracket 88 mounts the manifold assembly 32 to the filling system 10 with the manifolds 36 and 38 overlying the circular rail 16.

Figures 9, 10, 11:
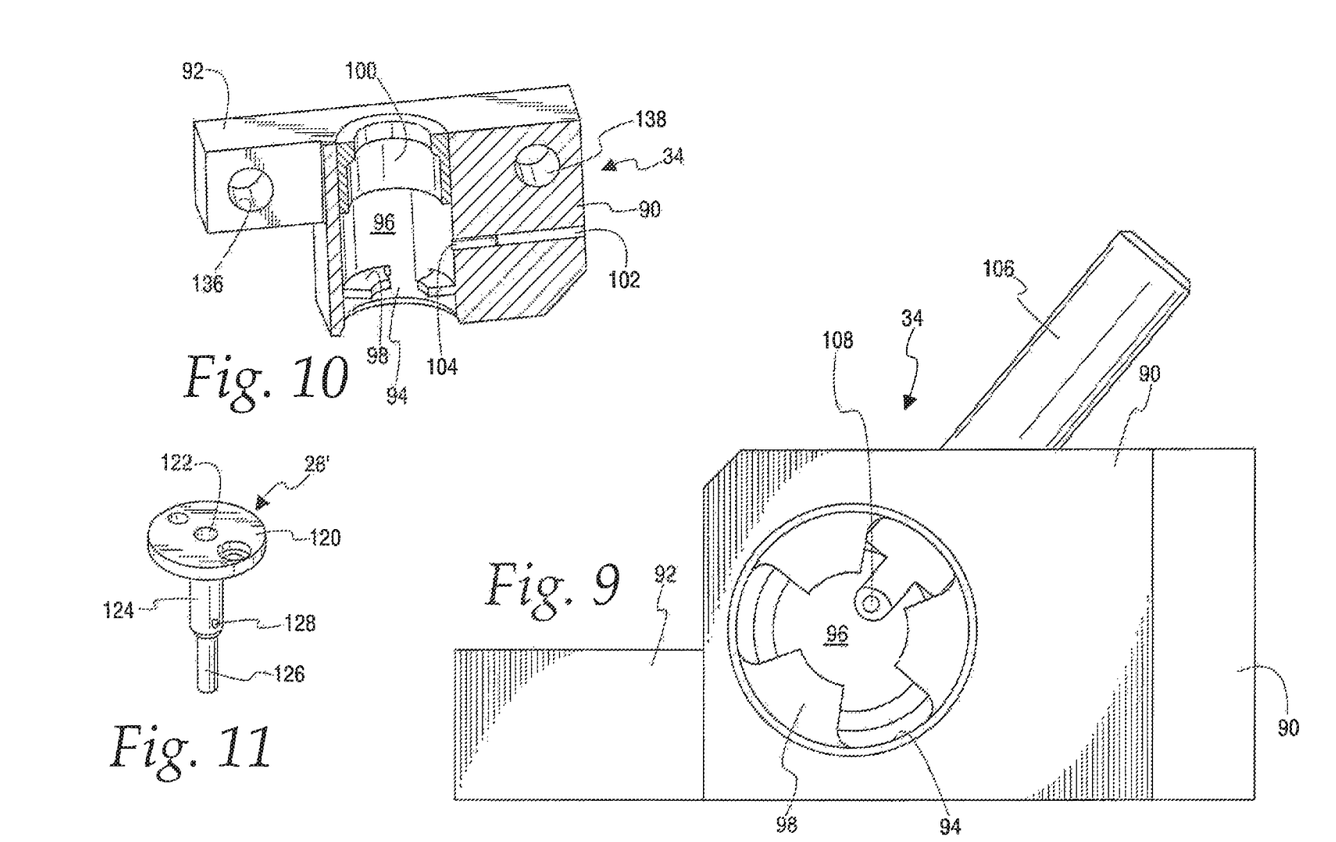
FIG. 9 is a bottom plan view of a stoppering block of the purging apparatus.
FIG. 10 is a sectional view of the stoppering block.
FIG. 11 is a perspective view of a modified funnel used with the purging apparatus.

The stoppering block 34 is shown in FIGS. 9 and 10. The stoppering block 34 comprises a metal body 90 which is generally rectangular in shape and including a projecting member 92. A cylindrical through bore 94 extends vertically through the metal body 90 defining a capping chamber 96. The bore 94 is sized to receive the bushing 18. A notched flat annular ring 98 extends across the capping chamber 96 proximate a bottom end of the cylindrical through bore 94. An annular ring 100 is pressed in place at a top end of the through bore 94 to narrow the top opening to accommodate a funnel, as described below. A transverse through opening 102 extends through the body 90 communicating with a first nozzle 104 opening into the capping chamber 96 above the ring 98. A tube 106 extends into the body 90 having a distal, downwardly facing second nozzle 108 off-center in the capping chamber 96. Referring also to FIG. 5, a flood inlet port 110 is mounted to the body 90 and is in communication with the through opening 102. A stream inlet port 112 is in communication with the tube 106.

Referring to FIG. 11, a funnel 28' is illustrated. The funnel 28' is similar to the funnel 28, see FIG. 2, but adapted for use with the purging system 32. Particularly, the funnel 28 comprises an upper flange 120 having a central opening 122 in communication with a tubular wall 124 extending downwardly therefrom. The tubular wall 124 narrows at a bottom end 126. In accordance with the invention, through openings 128 are provided in the tubular wall 124.

The stoppering block 34 is mounted within the manifold assembly 32 between the first manifold 36 and second manifold 38, see FIGS. 3-5, using bolts 132 and 134 received in respective openings 136 and 138 in the body 90 and projecting member 92, The capping chamber 96 is positioned above the space between the manifold bottom wall ends 70 and 78.

The operation of the filling system 10 including the purging system 32 is now described. The rotary dial machine 12, in pertinent part, indexes the bushings 18 between a filling position at the filling station 22 and a capping position at the capping station 24, as generally shown in FIG. 4. Each bushing 18 is loaded with a medical vial V to be filled and capped. Suitable apparatus in the rotary dial machine 12 lifts the bushings 18, and thus the vials V, for various options to be performed. Initially, at the filling station 22, the bushing 18 is lifted to the position shown in FIG. 8 wherein it is received in the lower filling chamber 54. The relevant structure at the filling station 22 includes a bracket 130, see FIGS. 3-5, supporting a downwardly depending tube 138 housing a hypodermic filling nozzle 134 shown in FIG. 8. A spacer 136 maintains the filling nozzle 134 centered in the vial V.

Prior to the bushing 18 being raised, the non-reactive gas supplied at the first manifold inlet port 62 exits the filling station outlet ports 64 and 66 and is directed into the lower filling chamber 54 and the upper filling chamber 60. Thus, the vial V is lifted into a chamber that is being purged with, for example, nitrogen. The number, diameter and location of the filling station outlet ports 64 and 66 is arranged to increase nitrogen concentration in and around the vial V thereby lowering the oxygen content in the vial V. The nitrogen purge, particularly via the outlet port 66, continues while the vial is being filled, see FIG. 8.

After filling, the bushing 18 is lowered below the manifold assembly 32 to the position shown in FIG. 4. The circular rail 16 is then rotated to move the bushing 18 to the right, as viewed in FIG. 4. The first manifold 36 sits above the vials V being transferred and extends between the filling station 22 and the capping station 24. The transfer outlet ports 68, see FIGS. 6 and 7, in the manifold bottom wall 48 direct nitrogen into the enclosed area between the access panels 84 and 86. Simulations indicate that approximately half of the nitrogen introduced at the filling station 22 would be lost without the use of such transfer outlet ports 68. Again, the number, diameter and location of the transfer outlet ports 68 is arranged to increase the nitrogen concentration in and around the vial V while being transferred, again lowering oxygen content in the filled vial V. The transfer outlet ports 68 are individually arranged so that the total nitrogen flow is directed in a balanced manner to provide the greatest benefit.

As described above, the stoppering block 34 includes the first nozzle 104 and the second nozzle 108 to continue the oxygen purging during the capping operation. As described herein, the stoppering block 34 uses turbulent flow of nitrogen to improve the purging. This is done using the dual nozzles.

In accordance with the invention, the first nozzle 104 is adapted to produce a flood zone of nitrogen. The second nozzle 108 produces a stream of nitrogen through the flood zone directed into the filled vial V. The second nozzle 108 is sized and placed very precisely and an optimum ratio of flood volume flow to nozzle stream volume flow has been analyzed so that the purging process is most effective. It has been determined that a lower limit of between 3:1 and 4:1 of flood volume to nozzle volume may be used. Subsequent testing indicates that a ratio of about 5:1 is optimum. This ratio and total flow can be adjusted as necessary during operation.

Figure 12:
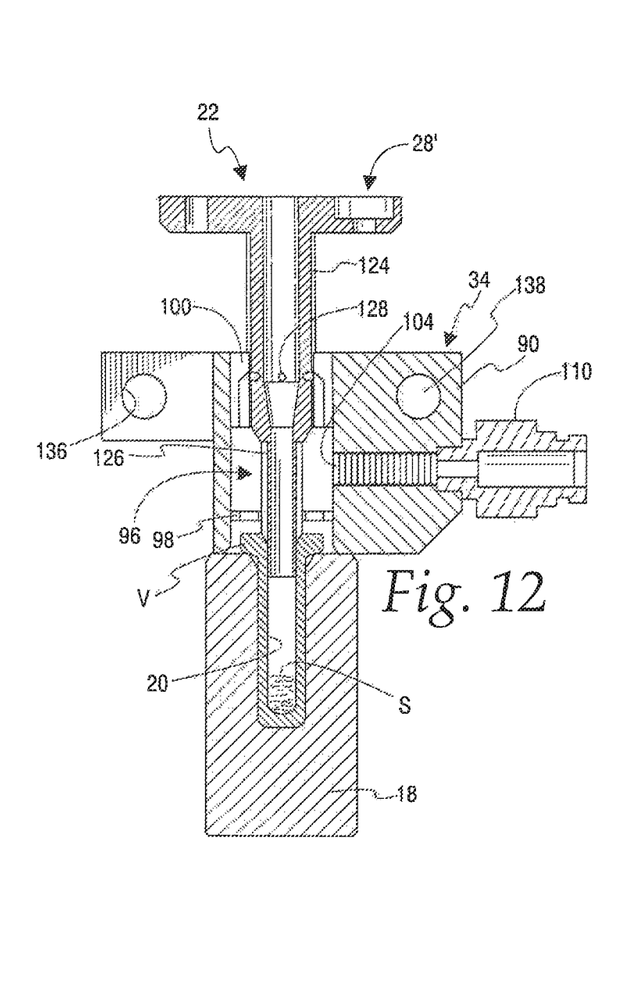
FIGS. 12 and 13 are sectional views illustrating the purging performed at the capping station.
Figure 13:
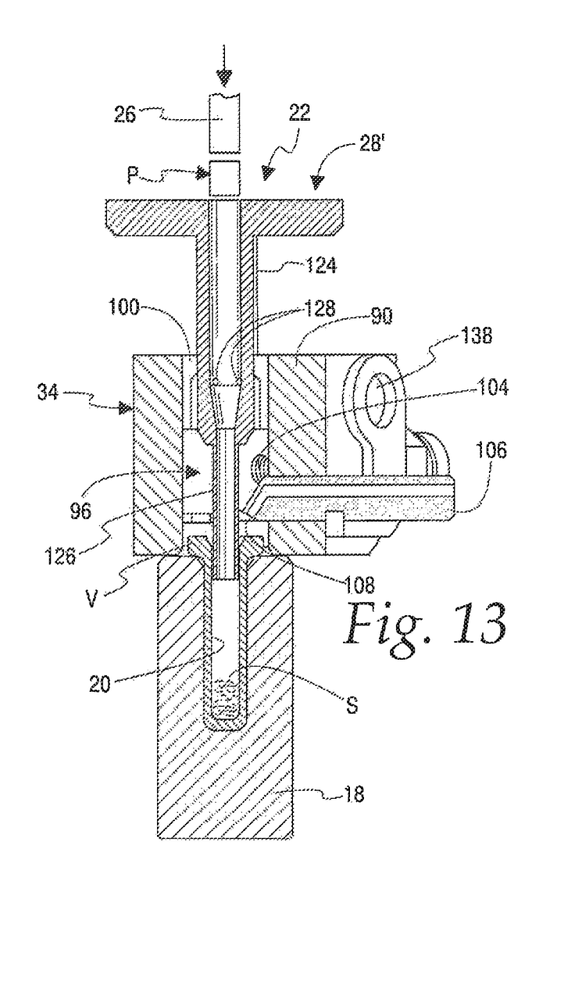

The purging operation at the capping station 24 is described referencing that illustrated in FIGS. 12 and 13. Prior to the bushing 18 entering the capping station 24, the bushing 18 is below the stoppering block 34 and the funnel 28' is above the stoppering block 34. Nitrogen is supplied to the inlet ports 110 and 112. A flood of nitrogen exits the first nozzle 104 and a stream of nitrogen exits the second nozzle 108. The nitrogen fills the capping chamber 96 and exits the top and bottom to push air out. The bushing 18 is then raised until it abuts a lower end of the stoppering block 34, see FIGS. 12 and 13. The top of the vial V extends slightly into the capping chamber 96 but is below the notched ring 98. Simultaneously, the funnel 28' is lowered into the position shown in FIGS. 12 and 13 wherein the funnel tube distal end 126 extends into a top of the filled vial V. As noted, the vial V contains a volume of solution S. During the time that the funnel 28' is being lowered, the nitrogen purge is introduced as a flood volume via the first nozzle 104 and the stream volume via the second nozzle 108 which is directed into the top of the vial V. To ensure that the funnel tube 124 is purged of oxygen, the three small holes 128 positioned in the tube 124 provide a back purge from below just before a stopper plug P, see FIG. 13, is pushed into the vial V. This back purge is sufficiently effective that flood flow can be reduced to keep the stopper plug located in its staging position. The stopper plug P is pushed through the funnel tube 124 into the vial V using the pusher 26.

The purge may be provided using a continuous flood of nitrogen. Alternatively, the flood may be intermittent or pulsed. The timing of pulsed or intermittent flow can be readily controlled without detrimental effect.

Owing to the use of the flood volume and stream volume as described, the process is adequate to fill the capping chamber 96 with nitrogen and push air out until the vial V is raised and as the funnel is lowered. Air entrained within the funnel 28' is purged through the openings 128 so that prior to inserting the plug P, the open space in the vial V above the solution S is substantially nitrogen as is the gas within the capping chamber 96 and the funnel tube 126 to minimize resultant oxygen within the capped vial.

As will be apparent, the precise size and location of the various outlet ports can be selected and adapted according to the design of the particular filling system. Likewise, some of the details of the purging system are specific to the design of the illustrated filling system. For example, while the rail 16 is circular, a linear structure or otherwise could be used, as will be apparent.

The exemplary filling system is adapted for filling glass vials for storing liquid drugs. The exemplary vials are about 1" long and intended to receive approximately 130 microliters of liquid. With such structure, tests have found that the resultant vial so produced may have oxygen on the order of 0.2%.

Thus, in accordance with the invention, a purging system and method are provided which direct a non-reactive gas, such as nitrogen, above and around the medical vial when the vial is positioned in the filling station, direct the flow of the non-reactive gas in an enclosed space through which the medical vial passes are being transferred between the filling station and the capping station, and directing flow of the non-reactive gas in a flood zone and a nozzle stream proximate the medical vial positioned in the capping station.

It will be appreciated by those skilled in the art that there are many possible modifications to be made to the specific forms of the features and components of the disclosed embodiments while keeping within the spirit of the concepts disclosed herein. Accordingly, no limitations to the specific forms of the embodiments disclosed herein should be read into the claims unless expressly recited in the claims. Although a few embodiments have been described in detail above, other modifications are possible.

The foregoing disclosure of specific embodiments is intended to be illustrative of the broad concepts comprehended by the invention.

The invention claimed is:

1. A method to purge oxygen and substitute a non-reactive gas in medical vials, comprising:
   providing a medical vial filling system adapted to transfer a medical vial between a filling station that fills the medical vial with a solution and a capping station that inserts a plug in the filled medical vial;
   directing a flow of a non-reactive gas in a space above and around the medical vial when the medical vial is positioned in the filling station;
   directing a flow of the non-reactive gas in an enclosed space through which the medical vial passes while being transferred between the filling station and the capping station; and
   directing a flow of the non-reactive gas in a flood zone surrounding a space above the medical vial when the medical vial is positioned in the capping station and in a nozzle stream directed into the medical vial when the medical vial is positioned in the capping station,
   wherein directing a flow of the non-reactive gas in a space above and around the medical vial when the medical vial is positioned in the filling station comprises the medical vial filling system including a manifold defining a chamber having outlet ports dispensing the non-reactive gas, wherein the medical vial filling system is configured to lift the medical vial into the chamber, the medical vial filling system including a filling nozzle for dispensing the solution into the medical vial while the non-reactive gas is dispersed in the chamber.

2. The method of claim 1 wherein the medical vial filling system comprises a stoppering block at the capping station and including a capping chamber for receiving the medical vial positioned at the capping station, the stoppering block comprising a stoppering inlet port, a first nozzle opening into the capping chamber and a second nozzle extending into the capping chamber and directed into the medical vial when the medical vial is positioned in the capping station to provide the flood zone and the nozzle stream.

3. A method to purge oxygen and substitute a non-reactive gas in medical vials, comprising:
   providing a medical vial filling system adapted to transfer a medical vial between a filling station that fills the medical vial with a solution and a capping station that inserts a plug in the filled medical vial;
   providing a manifold in the medical vial filling system disposed between the filling station and the capping station, the manifold including an inlet port and a plurality of output ports, the output ports positioned in a space above and around the medical vial when the medical vial is positioned in the filling station and in an enclosed space through which the medical vial passes while being transferred between the filling station and the capping station; and
   providing a supply of a non-reactive gas at the inlet port whereby the non-reactive gas flows out the manifold outlet ports to evacuate oxygen and substitute the non-reactive gas in the filled medical vial,
   wherein the manifold includes a filling chamber having select ones of the outlet ports and wherein the medical vial filling system is configured to lift the medical vial into the chamber, the medical vial filling system including a filling nozzle for dispensing the solution into the medical vial while the non-reactive gas is dispersed in the chamber.

4. The method of claim 3 further comprising providing a stoppering block at the capping station, the stoppering block comprising a stoppering inlet port, a first nozzle opening above the medical vial when the medical vial is positioned in the capping station and a second nozzle directed into the medical vial when the medical vial is positioned in the capping station, and
   providing a supply of a non-reactive gas at the stoppering inlet port to direct flow of the non-reactive gas in a flood zone surrounding a space above the medical vials when the medical vial is positioned in the capping station and in a stream directed into the medical vial when the medical vial is positioned in the capping station.

5. The method of claim 3 wherein the manifold includes select ones of the plurality of output ports positioned in a space over which the medical vial is transferred.

* * * * *